(12) United States Patent
Gill et al.

(10) Patent No.: US 7,842,485 B2
(45) Date of Patent: Nov. 30, 2010

(54) ENHANCED ALCOHOL TOLERANT MICROORGANISM AND METHODS OF USE THEREOF

(75) Inventors: Ryan T. Gill, Denver, CO (US); Michael D. Lynch, Westminster, CO (US); Tanya Warnecke, Boulder, CO (US)

(73) Assignee: The Regents of the University of Colorado, Denver, CO (US)

( * ) Notice: Subject to any disclaimer, the term of this patent is extended or adjusted under 35 U.S.C. 154(b) by 594 days.

(21) Appl. No.: 11/686,864

(22) Filed: Mar. 15, 2007

(65) Prior Publication Data

US 2007/0218533 A1    Sep. 20, 2007

Related U.S. Application Data

(60) Provisional application No. 60/782,831, filed on Mar. 15, 2006.

(51) Int. Cl.
  *C12P 7/06* (2006.01)
  *C12P 7/16* (2006.01)
  *C12N 15/74* (2006.01)
  *C12N 1/20* (2006.01)
(52) U.S. Cl. .................. 435/161; 435/160; 435/471; 435/252.33
(58) Field of Classification Search .............. None
  See application file for complete search history.

(56) References Cited

PUBLICATIONS

Yomano et al., J. Industrial Microbiol. Biotechnol. 1998, 20, 132-138, 1998.*
Weilbacher et al., Mol. Microbiol., 48, 3, 657-670, 2003.*

* cited by examiner

*Primary Examiner*—Nancy Vogel

(57) ABSTRACT

Embodiments of the present invention provide methods and compositions for microorganisms having increased alcohol tolerance. In certain embodiments, methods for using such microorganisms, and methods for identifying gene or genetic regions responsible for increased alcohol tolerance are contemplated.

13 Claims, 1 Drawing Sheet

ENHANCED ALCOHOL TOLERANT MICROORGANISM AND METHODS OF USE THEREOF

PRIORITY CLAIM

This application claims the benefit under 35 USC §119(e) of provisional U.S. patent application Ser. No. 60/782,831 filed on Mar. 15, 2006, which is incorporated herein in its entirety.

FEDERALLY FUNDED RESEARCH

The U.S. Government has a paid-up license in this invention and the right in limited circumstances to require the patent owner to license others on reasonable terms as provided for by the terms of Grant No. BES 0228584 awarded by the National Science Foundation.

FIELD OF THE INVENTION

The present invention relates to microorganisms having increased alcohol tolerance or resistance relative to a wild type microorganism, methods for using such microorganisms, and methods for identifying genes or genetic regions responsible for increased alcohol tolerance.

BACKGROUND OF THE INVENTION

Many useful chemicals can be toxic to the platform organisms proposed to toxicity, by regulating the transcription of 'stress' genes to either enhance or decrease the levels of certain gene products. *Escherichia coli* is a well studied microorganism with a completed genome sequence commonly used in the chemical industry. However, approximately 60% of predicted genes in the genome have unknown function.

Ethanol is a commodity chemical with an annual market of $15 billion and a current production of 2 billion gallons in the United States alone. It is used to make plastics, fibers, resins, and also as a renewable energy source to reduce the national dependence on foreign nonrenewable sources. Ethanol can be blended with gasoline up to 85% to create a cleaner burning fuel for automotives. Ethanol is commonly produced from fermentation of simple sugars or corn fibers. The first successful report of using recombinant *Escherichia coli* to produce ethanol was in 1989. Subsequent innovations on the process have lead to extremely high titers. Unfortunately, increased alcohol concentrations have shown to be toxic to microorganisms, limiting the production possibilities.

Therefore, there is a need for increased tolerance of microorganisms, such as *E. coli*, to alcohol in order to improve microbial production processes of ethanol.

SUMMARY OF THE INVENTION

Certain embodiments of the present invention provide for a modified microorganism having increased alcohol tolerance relative to its wild type and/or control type. In one embodiment, the modified microorganism is *E. coli*. In accordance with these embodiments, some modified *E. coli* have minimum ethanol bactericidal concentration of at least about 17% v/v for 99.99% *E. coli* death.

Another embodiment of the present invention provides for an *E. coli* that has been modified to increase expression of a genetic region including, but not limited to, yfdE, yhhL, yhhM, csrC, and a combination thereof, whereby alcohol tolerance is enhanced. In one particular embodiment, the alcohol is ethanol. In one embodiment, the increased expression is accomplished through increased copy numbers of the gene region. In another embodiment, increased expression of a genetic region, includes but is not limited to, upregulation of a genetic region. In other particular embodiments, the upregulation can be further enhanced by certain genetic manipulations.

Certain embodiments provide for a method for producing ethanol using a modified microorganism. In accordance with these embodiments, a method can provide for increased production of ethanol compared to a wild-type microorganism. Generally, the method includes but is not limited to:
culturing a microorganism under conditions sufficient to produce ethanol, wherein the microorganism can have enhanced expression of a genetic region selected from the group consisting of yfdE, yhhL, yhhM, csrC, and a combination thereof; and
recovering ethanol from the culture.

In accordance with these embodiments, an enhanced expression of a genetic region can be accomplished through increased copy numbers of the genetic region and/or upregulation of one or more of the genetic regions.

Certain embodiments herein provide for methods for identifying a genetic element in a genome of a microorganism. The genetic element can encode a polypeptide that is capable of confering increased alcohol tolerance in a microorganism. In accordance with these embodiments, these methods generally include, but are not limited to:
transforming or transfecting host cells with one or more vectors, wherein vectors include a plurality of libraries with varying predetermined fragment sizes of genomic DNA of the microorganism;
selecting transformed or transfected host cells having increased alcohol tolerance;
recovering vectors from selected cells; and
identifying by genome location, fragment inserts or predetermined sizes within the recovered vectors.

In one particular embodiment, the microorganism is *E. coli*.

Yet in another embodiment, the host cell is *E. coli*.

Certain embodiments provide for a method for enhancing alcohol tolerance of a microorganism including, but not limited to, modifying the microorganism to increase expression of a genetic region selected from the group consisting of yfdE, yhhL, yhhM, csrC, and a combination thereof.

In one particular embodiment, the microorganism is *E. coli*.

Still in another embodiment, the increased expression can be accomplished through increased copy numbers of the genetic region within the microorganism.

Yet in another embodiment, the increased expression can include, but is not limited to, enhanced upregulation of the gene region.

In certain particular embodiments, the alcohol is ethanol.

BRIEF DESCRIPTION OF THE DRAWINGS

The following drawings form part of the present specification and are included to further demonstrate certain embodiments of the present invention. The embodiments may be better understood by reference to one or more of these drawings in combination with the detailed description of specific embodiments presented herein.

DETAILED DESCRIPTION OF THE INVENTION

"Operative clone" of the gene region means any fragment within the gene region which is determined to confer a desired trait, including improved or enhanced tolerance to alcohols.

The terms "Improved tolerance, "improved resistance", "enhanced tolerance" and "enhanced resistance" are used interchangeably herein and refer to an improvement in a micro-organism's resistance to an alcohol and is observed as an increase (e.g., at least 5%) in minimum inhibitory concentration (MIC), or as an increased growth rate or final cell density or a decreased lag time for the transformants relative to the wild type E. coli or the control E. coli (transformed with the empty plasmid).

At any time only a small fraction of the genes in the E. coli genome are expressed. This expression profile is transient and changes due to the specific requirements of the cell at that time. In order to combat the toxic mechanisms of chemical stress the expression of genes can be regulated by the organism. For example, if the addition of an acid results in damaged genomic DNA, it is observed that the expression of the genes encoding proteins necessary in DNA repair are subsequently increased.

Parallel gene-trait mapping (PGTM) has been described as a high-throughput screening technique that allows for the simultaneous screening and sequencing of entire genomic libraries utilizing microarrays for example, microarrays (see Gill et al. PNAS, 2002, 99(10), 7033-7038, incorporated herein by reference in its entirety). A genomic library represents the entire genome using a collection of clones that individually express a portion of the genome. The genomic DNA of an organism can be randomly fragmented by digestion with restriction enzymes or by sonication. The fragmented DNA is joined, or ligated, with a cloning vector by formation of a phosphodiester bond between the vector and insert, creating a plasmid. The plasmids are then transformed into cells and collected.

PGTM is a genome-wide screening technique that has facilitated the identification of trait-conferring genes linked to antibiotic resistance, metabolite production, stress resistance, and specific growth rate. This method includes transforming a plasmid-based genomic library into wild type cells, culturing the transformants in a selective environment, and analyzing the resulting change in genotype using DNA microarrays. However, a difficulty that has not been addressed by PGTM and other traditional library screening methods is the identification of an individual trait-conferring gene or genetic region on an insert containing multiple genes or genetic elements.

Figure 1:
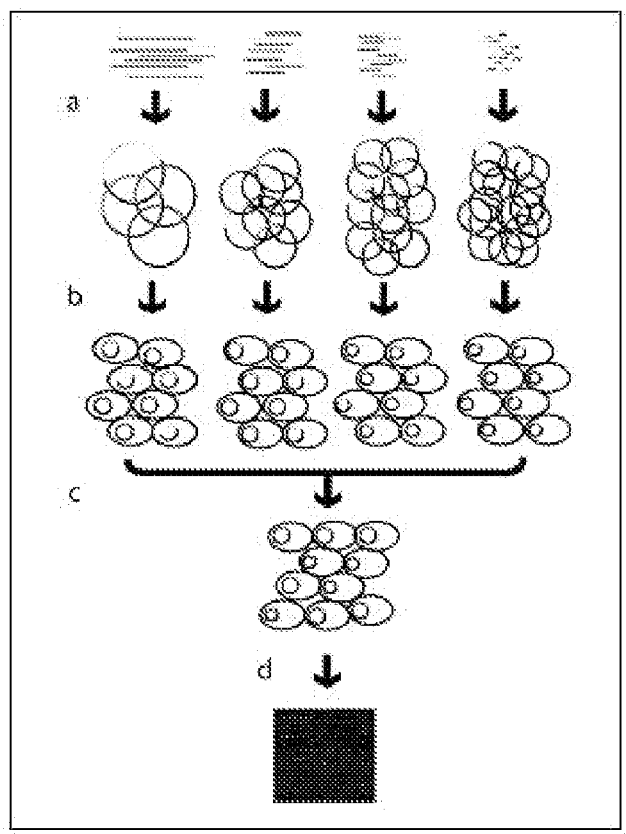
FIG. 1 is an exemplary schematic overview of Mixed Library Parallel Gene Trait Mapping (ML-PGTM)/Scalar Analysis of Library Enrichment method.

The Mixed Library Parallel Gene Trait Mapping (ML-PGTM) method shown in FIG. 1 now referred to as SCALES™ (SCalar Analysis of Library Enrichment, a genome-wide, multiscale approach to simultaneously measure the effect that the increased copy of each gene and/or operon has on a desired trait or phenotype; Gill et al. Nature Methods—4, 87-93 (2007), incorporated herein by reference in its entirety) was developed to correlate selective advantage to the overexpression of an individual gene or a combination of genes in an operon. This identification is facilitated by using a number of libraries with varying insert sizes. The range of insert sizes generate clones overexpressing both single genes as well as entire operons. By analyzing the plasmid composition of the selection population with microarrays or sequencing technology the trait-conferring gene(s) can be separated from those with insignificant contributions to stress tolerance. Those where a trait-conferring gene or trait-conferring genetic region has significant contributions to stress tolerance of a microorganism a can be further identified and/or isolated.

"Fragment bank of genomic DNA" or fragment library refers to a collection of genomic fragments of a microorganism. In certain embodiments, a library can include, but is not limited to fragments of specific sizes (e.g. nucleotide length). In certain particular embodiments, it is generally desired that the fragments are all substantially of the same size with little variation, as is described in U.S. Ser. No. 60/611,377, incorporated herein by reference in its entirety. The banks preferably also contain minimal numbers of fragment chimeras. Consistent size and minimal chimeras are necessary for more accurate final mathematical analysis of fragments in selected transformants. In certain particular embodiments, the fragments are inserted into vectors such as plasmids in sufficient number to be representative of the genome.

Certain embodiments provide methods for enhancing production of alcohols, such as ethanol, in biorefinery microorganisms, for example, E. coli. Exemplary alcohols for which enhanced production can be obtained include, but are not limited to, ethylene glycol, propylene glycol, polyethylene glycol, polypropylene glycol, poly(ethylene glycol/propylene glycol), 1,3-propanediol, 1,2-butanediol, 2,3-butanediol, 1,4-butanediol, 1,6-hexanediol, pinacol, glycerol, neopentylglycol, pentaerythritol, meso-hydrobenzoin, 1,2-cyclopentanediol, 1,2-cyclohexanediol, methanol, ethanol, isopropanol, n-propanol, n-butanol, isobutanol, sec-butanol, tert-butanol, n-pentanol, isopentanol, amyl alcohol, tert-pentanol, cyclopentanol, cyclohexanol, n-hexanol, n-heptanol, n-octanol, n-nonanol. n-decanol, n-dodecanol n-tetradecanol, n-hexadecanol, n-octadecanol, phenoxyethanol, benzyl alcohol, diphenyl carbinol, tetraphenylcarbinol and a combination thereof.

In accordance with these embodiments, a microorganism can be modified to reduce toxicity and or increase tolerance of the product to the host cell. Thus, increase quantities of a particular product can be produced by a microorganism (e g. large scale production of the product). For example, E. coli can be modified to increase expression of a gene region or genetic region including, but not limited to, yfdE, yhhL, yhhM, csrC, and a combination thereof. Without being bound by any theory, one belief is that expression of one or more of these genes or genetic regions affect alcohol stress tolerance of the microorganism such as E. coli. It is contemplated herein that these techniques may be applied to any prokaryotic cell, eukaryotic cell or archae. Thus, increased tolerance or decreased toxicity for production of a compound may be of use for these other cell types.

In one embodiment, a genetic region for enhancing alcohol tolerance in E. coli was determined using the method described in U.S. Provisional Patent Application No. 60/611, 377 and U.S. patent application Ser. No. 11/505,147 filed Aug. 15, 2006, also known as the Mixed-Library Gene Trait Mapping (ML-PGTM) technique or SCALEs, which is incorporated herein by reference in its entirety. This method is capable of mapping the effect of thousands of genes on a desired trait or phenotype. ML-PGTM is an improvement over PGTM (Parallel Gene Trait Mapping), in that ML-PGTM involves selections on a mixture of plasmid based genomic libraries of varying insert sizes, followed by microarray and mathematical analysis, which is used to quantitatively pinpoint the genetic element conferring the trait. The method effectively sequences thousands of inserts and identifies clones and subclones, which confer a trait. The analysis can also identify the selective advantage of each clone or subclone in a population giving valuable information regarding a gene's function.

As previously described (see U.S. Provisional Patent Application No. 60/611,377), microarray analysis of selected plasmid DNA, and wavelet based multiresolution analysis have been used to identify genetic elements relevant to enhance E. coli cell growth.

An exemplary overview of ML-PGTM is represented by FIG. 1. Briefly, several plasmid libraries were constructed with the DNA to be screened. These libraries were of predetermined insert sizes. In one embodiment, inserts were increased by a multiple of two for simplified subsequent mathematical analyses. These libraries were individually transformed into the cell line to be screened. Transformed populations were mixed and subjected to selection for a desired trait, e.g., resistance to ethanol toxicity or increase tolerance to ethanol production. Enriched plasmids were purified from the selected population, labeled and hybridized to a DNA micro-array, e.g., the Affymetrix E. coli Antisense Gene Chip array. Microarray probe level signals were plotted as a function of genome position. This signal was then subjected to a wavelet-based multi-resolution analysis, which decomposes the signal into scales or the signal contribution from each of the defined sized libraries.

In one exemplary method, as described in detail in the Examples, the ML-PGTM/SCALEs method as applied to the trait of enhanced ethanol resistance in E. coli, revealed that genes yfdE, yhhL, yhhM, and csrC, and operative clones therein were responsible for the enhanced ethanol resistance.

Another embodiment of the present invention provides a method for enhancing a desired trait in a microorganism by first identifying the responsible genetic element or insert according to the ML-PGTM/SCALEs method, and modifying the microorganism to increase the expression of the responsible genetic element. In accordance with this embodiment, modification can be done using methods known in the art, including transformation or transfection of the responsible genetic element or insert into the host cell by, e.g., electroporation, chemical treatment, conjugation, transduction, etc. Alternatively, a modification can also be done using techniques known in the art for genetically engineering the promoter region within the host organism or through homologous recombination with an engineered version of the gene under the control of an inducible or constitutive promoter. Further, the modification can be accomplished through the abolition of any negative regulation upon any one of the yfdE, yhhL, yhhM, and csrC genes.

In another embodiment, microorganism resistance to alcohols can be accomplished by modifying the microorganism to increase expression of one or more of yfdE, yhhL, yhhM, and csrC genes. In accordance with this embodiment, the modified microorganism can be cultured under conditions permitting the production of ethanol; and subsequently recovering ethanol from the culture. Methods for recovering ethanol from the culture are well known to one skilled in the art. In one particular embodiment, the microorganism can be E. coli and the alcohol can be ethanol.

In certain embodiments, it is contemplated that the enhancement of resistance to alcohols in a first species or strain of microorganism can involve the use of one or more yfdE, yhhL, yhhM, and csrC gene homologs from another species or strain. Moreover, increased resistance can involve the use of such homologs having at least 30% homology (or more preferably 50%, 60%, 70%, 80% or 90% homology) to the E. coli yfdE, yhhL, yhhM, or csrC gene region, if the homolog retains the function of enhancing alcohol resistance in the microorganism by at least 10%, and preferably by 20%, 30%, 40%, or 50%. Increased resistance in a microorganism can also be effected using one or more of the mutated or modified yfdE, yhhL, yhhM, and csrC gene regions, where the mutation or modification can involve methylation, halogenation and the like, provided that the mutated or modified gene region retains the function of enhancing alcohol resistance in the micro-organism by at least 10%, and preferably by 20%, 30%, 40%, or 50%.

In other embodiments, increased resistance to alcohols such as ethanol in modified microorganisms can be assayed by culturing the transformants in suitable media containing predetermined concentrations of ethanol or other alcohols, determining minimum inhibitory concentrations and constructing growth curves of the transformants in the presence of ethanol or other alcohols. Growth curves and inhibitory concentrations are compared to wild type E. coli and/or control E. coli (transformed with only the empty plasmid). Increased resistance is observed as an increase in MIC (minimum inhibitory concentration) or as an increased growth rate or final cell density or a decreased lag time for the transformants relative to the wild type E. coli or the control E. coli (transformed with the empty plasmid). The increase in the MIC can be about 5, 10, 20, 30, 40, 50, 60, 75, 80, 90, 100, 125, 150, 200, 400, or 600 percent over the wild type E. coli and/or control E. coli. In certain embodiments, the increase in MIC can be about 5%, or about 10%, or about 25%, or about 50%, or about 100%, or about 200% over the wild type E. coli and/or control E. coli.

Another aspect of the present invention comprises E. coli that has been modified to increase the expression of one or more of the yfdE, yhhL, yhhM, and csrC regions, whereby alcohol tolerance is enhanced. As discussed previously, the modification to increase expression can be accomplished by increasing copy number of one or more of such gene regions, or by upregulation of expression of one or more of such gene regions.

Still another aspect of the present invention comprises a method of enhancing production of ethanol in a microorganism that produces ethanol by modifying the microorganism to enhance expression of one or more of the yfdE, yhhL, yhhM, and csrC regions; culturing the modified microorganism under conditions permitting the production of ethanol; and recovering ethanol from the culture. Methods for recovering ethanol from the culture are well known to one skilled in the art.

The ML-PGTM/SCALEs technique was previously shown as capable of being used for identification of single open reading frames, as well as larger fragments, such as operons, that amplify a desired trait or phenotype. As specifically described in U.S. Provisional Patent Application No. 60/611, 377, the method was used to select E. coli transformants with increased growth rates in minimal media using genomic libraries with inserts of predetermined sizes, e.g., 0.5 kb, 1 kb, 2 kb, 4 kb and 8 kb. Microarrays and their subsequent analysis identified smaller and larger genetic elements that were responsible for the increased growth rate. A detailed analysis of the microarray results can project growth rates associated with each scale and position across the entire genome, providing genome wide trait mapping.

Additional objects, advantages, and novel features herein will become apparent to those skilled in the art upon examination of the following examples thereof, which are not intended to be limiting.

Nucleic Acids

As described herein, an aspect of the present disclosure concerns isolated nucleic acids and methods of use of isolated nucleic acids. In certain embodiments, the nucleic acid sequences disclosed herein have utility as hybridization probes or amplification primers. These nucleic acids may be used, for example, in diagnostic evaluation of tissue samples. In certain embodiments, these probes and primers consist of oligonucleotide fragments. Such fragments should be of sufficient length to provide specific hybridization to a RNA or DNA tissue sample. The sequences typically will be 10-20 nucleotides, but may be longer. Longer sequences, e.g., 40, 50, 100, 500 and even up to full length, are preferred for certain embodiments.

Nucleic acid molecules having contiguous stretches of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75 80, 85, 90, 95, 100, 125, 150, 175, 200, 250, 300, 400, 500, 600, 750, 1000, 1500, 2000, 2500 or more nucleotides from a sequence selected from the disclosed nucleic acid sequences are contemplated. Molecules that are complementary to the above mentioned sequences and that bind to these sequences under high stringency conditions also are contemplated. These probes will be useful in a variety of hybridization embodiments, such as Southern and Northern blotting.

The use of a hybridization probe of between 14 and 100 nucleotides in length allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained. One will generally prefer to design nucleic acid molecules having stretches of 20 to 30 nucleotides, or even longer where desired. Such fragments may be readily prepared by, for example, directly synthesizing the fragment by chemical means or by introducing selected sequences into recombinant vectors for recombinant production.

Accordingly, the nucleotide sequences herein may be used for their ability to selectively form duplex molecules with complementary stretches of genes or RNAs or to provide primers for amplification of DNA or RNA from tissues. Depending on the application envisioned, one may desire to employ varying conditions of hybridization to achieve varying degrees of selectivity of probe towards target sequence.

For applications requiring high selectivity, one will typically desire to employ relatively stringent conditions to form the hybrids, e.g., one will select relatively low salt and/or high temperature conditions, such as provided by about 0.02 M to about 0.10 M NaCl at temperatures of about 50° C. to about 70° C. Such high stringency conditions tolerate little, if any, mismatch between the probe and the template or target strand, and would be particularly suitable for isolating specific genes or detecting specific mRNA transcripts. It is generally appreciated that conditions can be rendered more stringent by the addition of increasing amounts of formamide.

For certain applications, lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM MgCl2, 10 mM dithiothreitol, at temperatures between approximately 20° C. to about 37° C. Other hybridization conditions utilized could include approximately 10 mM Tris-HCl (pH 8.3), 50 mM KCl, 1.5 µM MgCl2, at temperatures ranging from approximately 40° C. to about 72° C.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, calorimetric indicator substrates are known which can be employed to provide a detection means visible to the human eye or spectrophotometrically, to identify specific hybridization with complementary nucleic acid-containing samples.

In general, it is envisioned that the hybridization probes described herein will be useful both as reagents in solution hybridization, as in PCR, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface to remove non-specifically bound probe molecules, hybridization is detected, or even quantified, by means of the label.

Methods disclosed herein are not limited to the particular probes disclosed and particularly are intended to encompass at least nucleic acid sequences that are hybridizable to the disclosed sequences or are functional sequence analogs of these sequences. For example, a partial sequence may be used to identify a structurally-related gene or the full length genomic or cDNA clone from which it is derived. Those of skill in the art are well aware of the methods for generating cDNA and genomic libraries which can be used as a target for the above-described probes (Sambrook et al., 1989).

For applications in which the nucleic acid segments of the present invention are incorporated into vectors, such as plasmids disclosed herein, these segments may be combined with other DNA sequences, such as promoters, polyadenylation signals, restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol.

DNA segments encoding a specific gene may be introduced into recombinant host cells and employed for expressing a specific structural or regulatory protein. Alternatively, through the application of genetic engineering techniques, subportions or derivatives of selected genes may be employed. Upstream regions containing regulatory regions such as promoter regions may be isolated and subsequently employed for expression of the selected gene.

Where an expression product is to be generated, it is possible for the nucleic acid sequence to be varied while retaining the ability to encode the same product. Reference to the codon chart, provided above, will permit those of skill in the art to design any nucleic acid encoding for the product of a given nucleic acid.

Plasmid Preparations

Plasmid preparations and replication means are well known in the art. See for example, U.S. Pat. Nos. 4,273,875 and 4,567,146 incorporated herein their entirety. Some embodiments of the present invention include providing a portion of genetic material of a target microorganism and inserting the portion of genetic material of a target microorganism into a plasmid for use as an internal control plasmid.

Amplification

Embodiments of the present invention include providing conditions that facilitate amplification of at least a portion of a target genetic material. However, it should be appreciated that the amplification conditions of embodiments of the present invention are not necessarily 100% specific.

The embodiments of the present invention include any method for amplifying at least a portion of a microorganism's genetic material (such as Polymerase Chain Reaction (PCR), Real-time PCR (RT-PCR), NASBA (nucleic acid sequence based amplification)). In one embodiment, Real time PCR (RT-PCR) can be a method for amplifying at least a portion of a target microorganism's genetic material while simultaneously amplifying an internal control plasmid for verification of the outcome of the amplification of a microorganism's genetic material.

While the scope herein includes any method (for example, Polymerase Chain Reaction, i.e., PCR, and nucleic acid sequence based amplification, i.e., NASBA) for amplifying at least a portion of the microorganism's genetic material, for one example, the present invention describes embodiments in reference to PCR technique.

Amplification of a genetic material, e.g., DNA, is well known in the art. Methods include providing conditions that would allow co-amplification of an internal control plasmid's portion of a microorganism's genetic material and a portion of the microorganism's genetic material of a test sample, if the target microorganism is present in the sample and the conditions for the method support the amplification of the internal control plasmid. In this manner, detection of the amplification products by a specific probe for each product of the internal control plasmid's portion of a microorganism's genetic material and a portion of the microorganism's genetic material is indicative of the presence of the microorganism in the sample and that the conditions for the amplification are working. Thus, a negative result indicative of absence of a target microorganism can be confirmed.

Typically, to verify the working conditions of PCR techniques, positive and negative external controls are performed in parallel reactions to the sample tubes to test the reaction conditions, for example using a control nucleic acid sequence for amplification. In some embodiments of the present invention, an internal control can be used to determine if the conditions of the RT-PCR reaction is working in a specific tube for a specific target sample. Alternatively, in some embodiments of the present invention, an internal control can be used to determine if the conditions of the RT-PCR reaction are working in a specific tube at a specific time for a specific target microorganism sample.

By knowing the nucleotide sequences of the genetic material in a target microorganism and in an internal control, specific primer sequences can be designed. In one embodiment of the present invention, at least one primer of a primer pair used to amplify a portion of genomic material of a target microorganism is in common with one of the primers of a primer pair used to amplify a portion of genetic material of an internal control such as an internal control plasmid. In one embodiment of the present invention, a primer is about, but not limited to 5 to 50 oligonucleotides long, or preferably about 10 to 40 oligonucleotides long or more preferably about 10 to 30 oligonucleotides long. Suitable primer sequences can be readily synthesized by one skilled in the art or are readily available from third party providers such as BRL (New England Biolabs), etc. Other reagents, such as DNA polymerases and nucleotides, that are necessary for a nucleic acid sequence amplification such as PCR are also commercially available.

Detection

The presence or absence of PCR amplification product can be detected by any of the techniques known to one skilled in the art. In one particular embodiment, methods of the present invention include detecting the presence or absence of the PCR amplification product using a probe that hybridizes to a particular genetic material of the microorganism. By designing the PCR primer sequence and the probe nucleotide sequence to hybridize different portions of the microorganism's genetic material, one can increase the accuracy and/or sensitivity of the methods disclosed herein.

While there are a variety of labelled probes available, such as radioactive and fluorescent labelled probes, in one particular embodiment, methods of the present invention use a fluorescence resonance energy transfer (FRET) labeled probe as internal hybridization probes. In one particular embodiment of the present invention, an internal hybridization probe is included in the PCR reaction mixture so that product detection occurs as the PCR amplification product is formed, thereby reducing post-PCR processing time. Roche Lightcycler PCR instrument (U.S. Pat. No. 6,174,670) or other real-time PCR instruments can be used in this embodiment of the present invention, e.g., see U.S. Pat. No. 6,814,934. PCR amplification of a genetic material increases the sensitivity of methods of the present invention to 101 organisms or less in comparison to about 105 microorganisms that are required in standard ELISA methods. In some instances, real-time PCR amplification and detection significantly reduce the total assay time so that test results may be obtained in about 12 hours. Accordingly, methods herein provide rapid and/or highly accurate results relative to the conventional methods and these results are verified by an internal control.

Nucleic Acid Amplification

In certain embodiments, DNA fragments can be introduced into the cells of interest by the use of a vector, which is a replicon in which another polynucleotide segment is attached, so as to bring the replication and/or expression to the attached segment. A vector can have one or more restriction endonuclease recognition sites at which the DNA sequences can be cut in a determinable fashion without loss of an essential biological function of the vector. Vectors can further provide primer sites (e.g. for PCR), transcriptional and/or translational initiation and/or regulation sites, recombinational signals, replicons, selectable markers, etc. Examples of vectors include plasmids, phages, cosmids, phagemid, yeast artificial chromosome (YAC), bacterial artificial chromosome (BAC), human artificial chromosome (HAC), virus, virus based vector, such as adenoviral vector, lentiviral vector, and other DNA sequences which are able to replicate or to be replicated in vitro or in a host cell, or to convey a desired DNA segment to a desired location within a host cell. The vector may be, for example, a phage, plasmid, viral, or retroviral vector. Retroviral vectors may be replication competent or replication defective. In the latter case, viral propagation generally will occur only in complementing host cells.

Polynucleotides may be joined to a vector containing a selectable marker for propagation in a host. If the vector is a virus, it may be packaged in vitro using an appropriate packaging cell line and then transduced into host cells.

Polynucleotide inserts may be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors can include at least one selectable marker. Exemplary markers can include, but are not limited to, dihydrofolate reductase, G418, glutamine synthase, or neomycin resistance for eukaryotic cell culture, and tetracycline, kanamycin or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells (e.g., Saccharomyces cerevisiae or Pichia pastoris (ATCC Accession No. 201178)); insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

In certain embodiments vectors of use for bacteria can include, but are not limited to, pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PA0815 (all available from Invitrogen, Carlbad, Calif.). Other suitable vectors are readily apparent to the skilled artisan.

Recombinant DNA technologies used for the construction of the expression vector are those known and commonly used by persons skilled in the art. Standard techniques are used for cloning, isolation of DNA, amplification and purification; the enzymatic reactions involving DNA ligase, DNA polymerase, restriction endonucleases are carried out according to the manufacturer's recommendations. These techniques and others are generally carried out according to Sambrook et al. (1989).

In certain embodiments, it is contemplated that host cells can contain the above-described vector constructs described herein, and additionally encompasses host cells containing nucleotide sequences herein that are operably associated with one or more heterologous control regions (e.g., promoter and/or enhancer) using techniques known of in the art. The host cell can be a higher eukaryotic cell, such as a mammalian cell (e.g., a human derived cell), or a lower eukaryotic cell, such as a yeast cell, or the host cell can be a prokaryotic cell, such as a bacterial cell. A host strain may be chosen which modulates the expression of the inserted gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., phosphorylation, cleavage) of proteins. Appropriate cell lines can be chosen to ensure the desired modifications and processing of the foreign protein expressed.

It is contemplated herein that certain embodiments herein also encompasses primary, secondary, and immortalized host cells of vertebrate origin, particularly mammalian origin, that have been engineered to delete or replace endogenous genetic material (e.g., the coding sequence), and/or to include genetic material (e.g., heterologous polynucleotide sequences) that is operably associated with polynucleotides herein, and which activates, alters, and/or amplifies endogenous polynucleotides. For example, techniques known in the art may be used to operably associate heterologous control regions (e.g., promoter and/or enhancer) and endogenous polynucleotide sequences via homologous recombination (see, e.g., U.S. Pat. No. 5,641,670, issued Jun. 24, 1997; International Publication Number WO 96/29411; International Publication Number WO 94/12650; Koller et al., Proc. Natl. Acad. Sci. USA 86:8932-8935 (1989); and Zijlstra et al., Nature 342:435-438 (1989), the disclosures of each of which are incorporated by reference in their entireties).

In other embodiments, various whole-genome methods can be used to analyze the nucleic acids. The methods usually in involve the detection of hybridization of genetic segments to detect the presence and level of the segments in the sample. Microarrays can be used, either spotted or synthesized on a surface. Methods involving beads, microbeads, magnetic beads or fiber bundles may also be employed. Commercial whole-genome gene expression microarrays can be obtained from Applied Biosystems, Affymetrix, Agilent, GE Healthcare, and Illumina.

Nucleic acids used as a template for amplification can be isolated from cells contained in the biological sample, according to standard methodologies. (Sambrook et al., 1989) The nucleic acid may be genomic DNA or fractionated or whole cell RNA. Where RNA is used, it may be desired to convert the RNA to a complementary cDNA. In one embodiment, the RNA is whole cell RNA and is used directly as the template for amplification.

Pairs of primers that selectively hybridize to nucleic acids corresponding to specific markers are contacted with the isolated nucleic acid under conditions that permit selective hybridization. Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintilography of incorporated radiolabel or fluorescent label or even via a system using electrical or thermal impulse signals (Affymax technology; Bellus, 1994).

Primers

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences may be employed. Primers may be provided in double-stranded or single-stranded form, although the single-stranded form is preferred.

Template Dependent Amplification Methods

A number of template dependent processes are available to amplify the marker sequences present in a given template sample. One of the best known amplification methods is the polymerase chain reaction (referred to as PCR) which is described in detail in U.S. Pat. Nos. 4,683,195, 4,683,202 and 4,800,159, and in Innis et al., 1990, each of which is incorporated herein by reference in its entirety.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641 filed Dec. 21, 1990. Polymerase chain reaction methodologies are well known in the art. Other amplification methods are known in the art besides PCR such as LCR (ligase chain reaction), disclosed in European Application No. 320 308, incorporated herein by reference in its entirety.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids herein. Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases may be added as biotinylated derivatives for easy detection. A similar approach is used in SDA. Target specific sequences may also be detected using a cyclic probe reaction (CPR). In CPR, a probe having 3' and 5' sequences of non-specific DNA and a middle sequence of specific RNA is hybridized to DNA which is present in a sample. Upon hybridization, the reaction is treated with RNase H, and the products of the probe identified as distinctive products which are released after digestion. The original template is annealed to another cycling probe and the reaction is repeated. Still other amplification methods known in the art may be used with the methods described herein.

Separation Methods

Following amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation of amplified product or other molecules. There are many kinds of chromatography which may be used in the present invention: adsorption, partition, ion-exchange and molecular sieve, and many specialized techniques for using them including column, paper, thin-layer and gas chromatography (Freifelder, 1982).

Identification Methods

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products may then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, where the other member of the binding pair carries a detectable moiety.

In one embodiment, detection is by Southern blotting and hybridization with a labeled probe. The techniques involved in Southern blotting are well known to those of skill in the art and may be found in many standard books on molecular protocols.

In general, prokaryotes used for cloning DNA sequences in constructing the vectors useful herein can include but are not limited to, any gram negative bacterias such as E. coli strain K12. Other microbial strains which may be used include P. aeruginosa strain PAO1, and E. coli B strain. These examples are illustrative rather than limiting. Other example bacterial hosts for constructing a library include but are not limited to Aeromonas, Acetobacter, Agrobacterium, Alcaligenes, Azorizobium, Bartonella, Bordetella, Brucella, Burkholderia, Caulobacter, Escherichia, Erwinia, Hyphomicrobium, Methylobacillus, Methybacterium, Mehylophilus, Pseudomonus, Paracoccus, Rhizobium, Ralstonia, Rhodobacter, Salmonella, Vibrio and Xanthomonas.

Prokaryotic cells also can be used for expression. The aforementioned strains, as well as E. coli W3110 and other enterobacteriaceae such as Salmonella typhimurium or Serratia marcescans, and various pseudomonas species can be used.

In general, plasmid vectors containing promoters and control sequences which are derived from species compatible with the host cell are used with these hosts. The vector ordinarily carries a replication site as well as one or more marker sequences which are capable of providing phenotypic selection in transformed cells. For example, a PBBR1 replicon region which is useful in many Gram negative bacterial strains or any other replicon region that is of use in a broad range of Gram negative host bacteria can be used in the present invention.

Promoters suitable for use with prokaryotic hosts illustratively include the β-lactamase and lactose promoter systems. In other embodiments, expression vectors used in prokaryotic host cells may also contain sequences necessary for efficient translation of specific genes encoding specific mRNA sequences that can be expressed from any suitable promoter. This would necessitate incorporation of a promoter followed by ribosomal binding sites or a Shine-Dalgarno (S.D.) sequence operably linked to the DNA encoding the mRNA.

Construction of suitable vectors containing the desired coding and control sequences employ standard ligation techniques. Isolated plasmids or DNA fragments are cleaved, tailored, and religated in the form desired to form the plasmids required.

For analysis to confirm correct sequences in plasmids constructed, the ligation mixtures are used to transform a bacteria strain such as E. coli K12 and successful transformants selected by antibiotic resistance such as tetracycline where appropriate. Plasmids from the transformants are prepared, analyzed by restriction and/or sequenced.

Host cells can be transformed with expression vectors and cultured in conventional nutrient media modified as is appropriate for inducing promoters, selecting transformants or amplifying genes. The culture conditions, such as temperature, pH and the like, are those previously used with the host cell selected for expression, and will be apparent to the ordinarily skilled artisan.

"Transformation" refers to the taking up of an expression vector by a host cell whether or not any coding sequences are in fact expressed. Numerous methods of transfection are known to the ordinarily skilled artisan, for example, Ca salts and electroporation. Successful transformation is generally recognized when any indication of the operation of this vector occurs within the host cell.

In order to facilitate understanding of the following examples certain frequently occurring methods and/or terms will be described.

Digestion of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Recovery or isolation of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally (Lawn, R. et al., Nucleic Acids Res. 9: 6103 6114 [1981], and Goeddel, D. et al., Nucleic Acids Res. 8: 4057 [1980]).

Dephosphorylation refers to the removal of the terminal 5' phosphates by treatment with bacterial alkaline phosphatase (BAP). This procedure prevents the two restriction cleaved ends of a DNA fragment from "circularizing" or forming a closed loop that would impede insertion of another DNA fragment at the restriction site. Procedures and reagents for dephosphorylation are conventional (Maniatis, T. et al., Molecular Cloning, 133 134 Cold Spring Harbor, [1982]). Reactions using BAP are carried out in 50 mM Tris at 68.degree. C. to suppress the activity of any exonucleases which may be present in the enzyme preparations. Reactions are run for 1 hour. Following the reaction the DNA fragment is gel purified.

Ligation refers to the process of forming phosphodiester bonds between two double stranded nucleic acid fragments (Maniatis, T. et al., Id. at 146). Unless otherwise provided, ligation may be accomplished using known buffers and conditions with 10 units of T4 DNA ligase ("ligase") per 0.5 .mu.g of approximately equimolar amounts of the DNA fragments to be ligated.

Filling or blunting refers to the procedures by which the single stranded end in the cohesive terminus of a restriction enzyme-cleaved nucleic acid is converted to a double strand. This eliminates the cohesive terminus and forms a blunt end. This process is a versatile tool for converting a restriction cut end that may be cohesive with the ends created by only one or a few other restriction enzymes into a terminus compatible with any blunt-cutting restriction endonuclease or other filled cohesive terminus. In one embodiment, blunting is accomplished by incubating around 2 to 20 µg of the target DNA in 10 mM $MgCl_2$, 1 mM dithiothreitol, 50 mM NaCl, 10 mM Tris (pH 7.5) buffer at about 37° C. in the presence of 8 units of the Klenow fragment of DNA polymerase I and 250 µM of each of the four deoxynucleoside triphosphates. The incubation generally is terminated after 30 min. phenol and chloroform extraction and ethanol precipitation As used interchangeably herein, the terms "nucleic acid molecule(s)", "oligonucleotide(s)", and "polynucleotide(s)" include RNA or DNA (either single or double stranded, coding, complementary or antisense), or RNA/DNA hybrid sequences of more than one nucleotide in either single chain or duplex form (although each of the above species may be particularly specified). The term "nucleotide" is used herein as an adjective to describe molecules comprising RNA, DNA, or RNA/DNA hybrid sequences of any length in single-stranded or duplex form. More precisely, the expression "nucleotide sequence" encompasses the nucleic material itself and is thus not restricted to the sequence information (e g. the succession of letters chosen among the four base letters) that biochemically characterizes a specific DNA or RNA molecule. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. The term "nucleotide" is also used herein to encompass "modified nucleotides" which comprise at least one modifications such as (a) an alternative linking group, (b) an analogous form of purine, (c) an analogous form of pyrimidine, or (d) an analogous sugar. For examples of analogous linking groups, purine, pyrimidines, and sugars see for example PCT publication No. WO 95/04064, which disclosure is hereby incorporated by reference in its entirety. Preferred modifications of the present invention include, but are not limited to, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta- D-mannosylqueosine, 5'-methoxycarboxymethyluracil, 5-methoxyuracil, 2-methylthio-N6-isopentenyladenine, uracil-5-oxyacetic acid (v) ybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl)uracil, and 2,6-diaminopurine. The polynucleotide sequences herein may be prepared by any known method, including synthetic, recombinant, ex vivo generation, or a combination thereof, as well as utilizing any purification methods known in the art. Methylenemethylimino linked oligonucleosides as well as mixed backbone compounds, may be prepared as described in U.S. Pat. Nos. 5,378,825; 5,386,023; 5,489,677; 5,602,240; and 5,610,289, which disclosures are hereby incorporated by reference in their entireties. Formacetal and thioformacetal linked oligonucleosides may be prepared as described in U.S. Pat. Nos. 5,264,562 and 5,264,564, which disclosures are hereby incorporated by reference in their entireties. Ethylene oxide linked oligonucleosides may be prepared as described in U.S. Pat. No. 5,223,618, which disclosure is hereby incorporated by reference in its entirety. Phosphinate oligonucleotides may be prepared as described in U.S. Pat. No. 5,508,270, which disclosure is hereby incorporated by reference in its entirety. Alkyl phosphonate oligonucleotides may be prepared as described in U.S. Pat. No. 4,469,863, which disclosure is hereby incorporated by reference in its entirety. 3'-Deoxy-3'-methylene phosphonate oligonucleotides may be prepared as described in U.S. Pat. No. 5,610,289 or 5,625,050 which disclosures are hereby incorporated by reference in their entireties. Phosphoramidite oligonucleotides may be prepared as described in U.S. Pat. No. 5,256,775 or 5,366,878 which disclosures are hereby incorporated by reference in their entireties. Alkylphosphonothioate oligonucleotides may be prepared as described in published PCT applications WO 94/17093 and WO 94/02499 which disclosures are hereby incorporated by reference in their entireties. 3'-Deoxy-3'-amino phosphoramidate oligonucleotides may be prepared as described in U.S. Pat. No. 5,476,925, which disclosure is hereby incorporated by reference in its entirety. Phosphotriester oligonucleotides may be prepared as described in U.S. Pat. No. 5,023,243, which disclosure is hereby incorporated by reference in its entirety. Borano phosphate oligonucleotides may be prepared as described in U.S. Pat. Nos. 5,130,302 and 5,177,198 which disclosures are hereby incorporated by reference in their entireties.

The term "upstream" is used herein to refer to a location which is toward the 5' end of the polynucleotide from a specific reference point.

The terms "base paired" and "Watson & Crick base paired" are used interchangeably herein to refer to nucleotides which can be hydrogen bonded to one another by virtue of their sequence identities in a manner like that found in double-helical DNA with thymine or uracil residues linked to adenine residues by two hydrogen bonds and cytosine and guanine residues linked by three hydrogen bonds (See Stryer, 1995, which disclosure is hereby incorporated by reference in its entirety).

The terms "complementary" or "complement thereof" are used herein to refer to the sequences of polynucleotides which is capable of forming Watson & Crick base pairing with another specified polynucleotide throughout the entirety of the complementary region. For the purpose of the present invention, a first polynucleotide is deemed to be complementary to a second polynucleotide when each base in the first polynucleotide is paired with its complementary base. Complementary bases are, generally, A and T (or A and U), or C and G. "Complement" is used herein as a synonym from "complementary polynucleotide", "complementary nucleic acid" and "complementary nucleotide sequence". These terms are applied to pairs of polynucleotides based solely upon their sequences and not any particular set of conditions under which the two polynucleotides would actually bind. Unless otherwise stated, all complementary polynucleotides are fully complementary on the whole length of the considered polynucleotide.

The terms "polypeptide" and "protein", used interchangeably herein, refer to a polymer of amino acids without regard to the length of the polymer; thus, peptides, oligopeptides, and proteins are included within the definition of polypeptide. This term also does not specify or exclude chemical or post-expression modifications of the polypeptides herein, although chemical or post-expression modifications of these polypeptides may be included excluded as specific embodiments. Therefore, for example, modifications to polypeptides that include the covalent attachment of glycosyl groups, acetyl groups, phosphate groups, lipid groups and the like are expressly encompassed by the term polypeptide. Further, polypeptides with these modifications may be specified as individual species to be included or excluded from the present invention. The natural or other chemical modifications, such as those listed in examples above can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance Creighton (1993); Seifter et al., (1990); Rattan et al., (1992)). Also included within the definition are polypeptides which contain one or more analogs of an amino acid (including, for example, non-naturally occurring amino acids, amino acids which only occur naturally in an unrelated biological system, modified amino acids from mammalian systems, etc.), polypeptides with substituted linkages, as well as other modifications known in the art, both naturally occurring and non-naturally occurring.

As used herein, the terms "recombinant polynucleotide" and "polynucleotide construct" are used interchangeably to refer to linear or circular, purified or isolated polynucleotides that have been artificially designed and which comprise at least two nucleotide sequences that are not found as contiguous nucleotide sequences in their initial natural environment. In particular, these terms mean that the polynucleotide or cDNA is adjacent to "backbone" nucleic acid to which it is not adjacent in its natural environment. Additionally, to be "enriched" the cDNAs will represent 5% or more of the number of nucleic acid inserts in a population of nucleic acid backbone molecules. Backbone molecules according to the present invention include nucleic acids such as expression vectors, self-replicating nucleic acids, viruses, integrating nucleic acids, and other vectors or nucleic acids used to maintain or manipulate a nucleic acid insert of interest. Preferably, the enriched cDNAs represent 15% or more of the number of nucleic acid inserts in the population of recombinant backbone molecules. More preferably, the enriched cDNAs represent 50% or more of the number of nucleic acid inserts in the population of recombinant backbone molecules. In a highly preferred embodiment, the enriched cDNAs represent 90% or more (including any number between 90 and 100%, to the thousandth position, e.g., 99.5%) of the number of nucleic acid inserts in the population of recombinant backbone molecules.

As used herein, the term "operably linked" refers to a linkage of polynucleotide elements in a functional relationship. A sequence which is "operably linked" to a regulatory sequence such as a promoter means that said regulatory element is in the correct location and orientation in relation to the nucleic acid to control RNA polymerase initiation and expression of the nucleic acid of interest. For instance, a promoter or enhancer is operably linked to a coding sequence if it affects the transcription of the coding sequence.

In one embodiment, the polynucleotides are at least 15, 30, 50, 100, 125, 500, or 1000 continuous nucleotides. In another embodiment, the polynucleotides are less than or equal to 300 kb, 200 kb, 100 kb, 50 kb, 10 kb, 7.5 kb, 5 kb, 2.5 kb, 2 kb, 1.5 kb, or 1 kb in length. In a further embodiment, polynucleotides herein comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides do not contain the coding sequence of more than 1000, 500, 250, 100, 75, 50, 25, 20, 15, 10, 5, 4, 3, 2, or 1 naturally occurring genomic flanking gene(s).

Procedures used to detect the presence of nucleic acids capable of hybridizing to the detectable probe include well known techniques such as Southern blotting, Northern blotting, dot blotting, colony hybridization, and plaque hybridization. In some applications, the nucleic acid capable of hybridizing to the labeled probe may be cloned into vectors such as expression vectors, sequencing vectors, or in vitro transcription vectors to facilitate the characterization and expression of the hybridizing nucleic acids in the sample. For example, such techniques may be used to isolate and clone sequences in a genomic library or cDNA library which are capable of hybridizing to the detectable probe as described herein.

Labels

Certain embodiments may involve incorporating a label into a probe, primer and/or target nucleic acid to facilitate its detection by a detection unit. A number of different labels may be used, such as Raman tags, fluorophores, chromophores, radioisotopes, enzymatic tags, antibodies, chemiluminescent, electroluminescent, affinity labels, etc. One of skill in the art will recognize that these and other label moieties not mentioned herein can be used in the disclosed methods.

Fluorescent labels of use may include, but are not limited to, Alexa 350, Alexa 430, AMCA (7-amino-4-methylcoumarin-3-acetic acid), BODIPY (5,7-dimethyl-4-bora-3a,4a-diaza-s-indacene-3-propionic acid) 630/650, BODIPY 650/665, BODIPY-FL (fluorescein), BODIPY-R6G (6-carboxyrhodamine), BODIPY-TMR (tetramethylrhodamine), BODIPY-TRX (Texas Red-X), Cascade Blue, Cy2 (cyanine), Cy3, Cy5,6-FAM (5-carboxyfluorescein), Fluorescein, 6-JOE (2'7'-dimethoxy-4'5'-dichloro-6-carboxyfluorescein), Oregon Green 488, Oregon Green 500, Oregon Green 514, Pacific Blue, Rhodamine Green, Rhodamine Red, ROX (6-carboxy-X-rhodamine), TAMRA (N,N,N',N'-tetramethyl-6-carboxyrhodamine), Tetramethylrhodamine, and Texas Red. Fluorescent or luminescent labels can be obtained from standard commercial sources, such as Molecular Probes (Eugene, Oreg.).

Examples of enzymatic labels include urease, alkaline phosphatase or peroxidase. Colorimetric indicator substrates can be employed with such enzymes to provide a detection means visible to the human eye or spectrophotometrically. Radioisotopes of potential use include 14 carbon, 3 hydrogen, 125 iodine, 32 phosphorus and 35 sulphur.

Vectors for Gene Expression

In certain embodiments, expression vectors can be employed to assay the functional effects of certain sequences such as a bi-directional, host-factor independent transcriptional terminators sequence. Expression can require appropriate signals be provided in the vectors, and which include various regulatory elements, such as enhancers/promoters from viral or mammalian sources that drive expression of the genes of interest in host cells. Bi-directional, host-factor independent transcriptional terminators elements may be incorporated into the expression vector and levels of transcription, translation, RNA stability or protein stability may be determined using standard techniques known in the art. The effect of the bi-directional, host-factor independent transcriptional terminators sequence may be determined by comparison to a control expression vector lacking the bidirectional, host-factor independent transcriptional terminators sequence, or to an expression vector containing a bidirectional, host-factor independent transcriptional terminators sequence of known effect.

Regulatory Elements

In certain embodiments, an expression construct or expression vector can be included in methods contemplated herein. In accordance with these embodiments, any type of genetic construct containing a nucleic acid coding for a gene product in which part or all of the nucleic acid coding sequence is capable of being transcribed. In one particular embodiment, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" can mean that the promoter is in the correct location and orientation in relation to the nucleic acid to control RNA polymerase initiation and expression of the gene.

Where a cDNA insert is employed, typically one can include a polyadenylation signal to effect proper polyadenylation of the gene transcript. A terminator is also contemplated as an element of the expression construct. These elements can serve to enhance message levels and to minimize read through from the construct into other sequences.

Reporter Genes

In certain embodiments of the present invention, the expression construct will contain a reporter gene whose activity may be measured to determine the effect of a bi-directional, host-factor independent transcriptional terminators element or other element. Conveniently, the reporter gene produces a product that is easily assayed, such as a colored product, a fluorescent product or a luminescent product. Many examples of reporter genes are available, such as the genes encoding GFP (green fluorescent protein), CAT (chloramphenicol acetyltransferase), luciferase, GAL (β-galactosidase), GUS (β-glucuronidase), etc. The reporter gene employed is not believed to be important, so long as it is capable of being expressed and its level of expression may be assayed. Further examples of reporter genes are well known to one of skill in the art, and any such known gene may be used in the practice of the claimed methods.

Data Analysis

In various embodiments, the data analysis used in the ML-PGTM/SCALEs method (U.S. patent application Ser. No. 11/231,018 filed Sep. 20, 2005, incorporated herein by reference in its entirety) provides a genome-wide, quantitative identification of genetic elements conferring or associated with a trait. The following discussion provides one non-limiting example of how data analysis may be performed in the ML-PGTM method.

Microarray Signal Extraction

Affymetrix *E. Coli* Antisense Gene Chip arrays (Affymetrix) were hybridized with genomic libraries containing different inserts of defined length and scanned according to the *E. Coli* expression protocol from Affymetrix, producing affymetrix.cel files. Raw chip signals were extracted from the Affymetrix files. Probe signals were extracted and grouped by affinity. These groupings were based on the predicted probe affinities suggested by Magnasco & Naef, (2003, Phys Rev E Stat Nonlin Soft Matter Phys. 68(1 Pt 1)).

The background for each probe was subtracted by a MAS 5.0 type algorithm, where the weighted average of the lowest 2% of signals from 16 chip sections were used as a measure of background.

The perfect match signal was robustly regressed against the PM-MM signals for each group. The intercept of this regression served as a measure of nonspecific signal for the probes in this group. This signal was subtracted from each probe.

Chips were normalized using a set of 5 positive control probe plasmids. These control concentrations were applied equally to each array in a range from 0 pM to 0.5 pM. Normalization was done by fitting signal intensity to a logarithmic function of the positive control probe concentration. These fit curves were used to estimate concentrations from each array for all probe signals.

Multiresolution Analysis

A Wavelet based multiresolution analysis was applied to the corrected probe signals from each chip. This was done using a modified Haar Scaling function. Rather than a direct averaging, a Tukey biweight was applied to achieve more robust estimates. The signal attributable to a given scale at a given position was calculated as the tukey biweight estimate of all probes within a half a scales distance in either direction from the position in question. This was done for 8000 bp, 4000 bp, 2000 bp, 1000 bp and 500 bp scales, if the density of probes in a given region permitted all scales to be calculated. At any position the scale signals were normalized such that their sum was equal to the original signal at that position. This original signal was estimated by the signal of the smallest scale available.

Growth rates for a given scale centered at a given position were calculated using a standard Monod equation, substituting the scale signals as estimations of concentrations.

Micro-Arrays

In particular embodiments, the methods disclosed herein may utilize one or more microarray devices for analysis of genetic elements. It is contemplated that any type of microarray known in the art may be used. A variety of nucleic acid microarrays are known and/or are commercially available. For example, *E. Coli* Antisense Gene Chip arrays (Affymetrix, Santa Clara, Calif.), may be of use in specific embodiments. Generally, microarrays will comprise ordered arrays of nucleic acids, such as nucleic acid probes, that are covalently or non-covalently attached to a chip surface (e.g., Schena, ed., "DNA Microarrays A Practical Approach," Oxoford University Press; Marshall et al. (1998) Nat. Biotechnol. 16:27-31; each incorporated herein by reference).

Kits

Certain embodiments concerns kits for use with the methods described herein. The kits can include but is not limited to, a suitable container means, one or more vectors, each vector capable of being used with bacterial cultures (e g. *E. coli*). In various embodiments, such kits may contain additional components of use for the amplification, hybridization and/or detection of vector sequences and or inserts, which components may include but not limited to two or more amplification primers, buffer, nucleotides, labels (such as fluorescent labels), labeled primers, polymerase, enzymes, enzyme substrates, control probes, control amplification templates, molecular weight standards or any other kit component known in the art.

Exemplary kits may further include a suitably aliquoted composition of the probes and/or primers, whether labeled or unlabeled, as may be used to prepare a standard curve for a detection assay. The components of the kits may be packaged either in aqueous media or in lyophilized form.

The container means of the kits can generally include at least one vial, test tube, flask, bottle, syringe or other container means, into which the probes and/or primers may be placed, and preferably, suitably aliquoted. Where an additional component is provided, the kit will also generally contain additional containers into which this component may be placed. The kits of the present invention will also typically include a means for containing the probes, primers, and any other reagent containers in close confinement for commercial sale. Such containers may include injection or blow-molded plastic containers into which the desired vials are retained.

The embodiments herein are further illustrated by the following examples and detailed protocols. However, the examples are merely intended to illustrate embodiments and are not to be construed to limit the scope herein. The contents of all references and published patents and patent applications cited throughout this application are hereby incorporated by reference

EXAMPLES

The following examples are included to illustrate various embodiments. It should be appreciated by those of skill in the art that the techniques disclosed in the examples which follow represent techniques discovered to function well in the practice of the claimed methods, compositions and apparatus. However, those of skill in the art should, in light of the present disclosure, appreciate that many changes may be made in the specific embodiments which are disclosed and still obtain a like or similar result without departing from the spirit and scope herein.

Genomic Library Construction

In one exemplary method, genomic DNA was extracted from *Escherichia coli* K12. This strain was chosen as it has a known genome sequence corresponding to readily available DNA microarray chips. The purified genomic DNA was partially digested using two restriction enzymes, Rsa1 and Alu1, in order to ensure entire genomic representation and a range of fragment sizes. The digestion product was then analyzed using agarose-gel electrophoresis. Fragments corresponding to 0.5, 1, 2, 4, and 8 kb in size were excised from the gel and purified.

In another exemplary method, two vectors were used in order to introduce and overexpress the purified genomic fragments into E. coli strains. The pSMART vector chosen is a low copy vector that replicates at 15-30 copies/cell which corresponds to moderate overexpression levels within the cell. This plasmid does not contain a promoter and relies on native transcription of the gene. The pEZseq vector used is a high copy vector that increases expression drastically due to replication levels of approximately 300-500 copies/cell. This plasmid contains an inducible promoter that could help identify genes leading to increased tolerance that are not normally expressed by the cell under stressful conditions. Both vectors confer resistance to a common antibiotic, kanamycin. This resistance is not native to E. coli and can be subsequently used to select for cells containing the vector.

In another exemplary method, each individual fragment size was ligated separately with the vectors to form plasmids, or a circular unit of DNA that replicates independently of the genomic DNA. The plasmids were then transformed, or introduced, into an electrocompetent E. coli strain using electroporation. A small volume of the transformants was cultured on LB+kanamycin plates. The plated colonies were then counted to ensure transformation efficiencies necessary for a representative library. Plasmid DNA was then extracted and purified from the transformants.

In accordance with these methods, insert sizes were confirmed by the use of two methods. First, PCR was performed on 8 individual colonies picked from dilution plates of each library size and vector. This method amplifies the DNA region extending from a primer sequence based on the vector itself. The amplified region therefore corresponds to the joined fragment. In addition to PCR, the purified plasmids were digested using an enzyme that cleaved on either side of the fragment. Both the PCR and digestion products were then analyzed using agarose-gel electrophoresis to confirm the expected fragment sizes.

Minimal Bactericidal Concentration (MBC) Determination

In one example, the MBC value was used to quantify the toxicity of the specific chemicals for each strain or clone. 100 mL of MOPS minimal media was inoculated at 1% from an overnight culture of a given E. coli strain or clone. Kanamycin was added to clone cultures containing the plasmids conferring resistance as described above. This culture was incubated until it had reached an $OD_{600}$ of 0.30 corresponding to a cell density within the exponential growth phase. The original culture was split into 5 mL cultures contained in 15 mL capped vials. The subcultures were then treated with ethanol over a range of 0-30% v/v and incubated at 37° C. for 1 hour.

Dilution cultures were inoculated to $10^{-4}$-$10^{-6}$ cell concentration of the subcultures and plated on LB in duplicate. Plates were then incubated at 37° C. for 18 hours. MBC values were defined as the lowest concentration necessary to kill 99.9% or 99.99% of the original inoculums and were determined by counting colony growth on dilution plates.

Library Selection and Sampling

Purified plasmid DNA from each library was introduced into MACH1 or W3110 E. coli by electroporation. The original cultures were combined and diluted to 100 ml with MOPS minimal media and incubated at 37° C. for 5 hours or until reaching an $OD_{600}$ of 0.30. The transformation culture was then split and treated with antibiotic at concentrations around and above the MBC value determined for Mach1 E. coli. The cultures were incubated for overnight at 37° C. in the presence of the antibiotic.

In another exemplary method, samples of the selection culture were spread onto LB+kanamycin plates and used to inoculate 5 mL LB+kanamycin overnight liquid cultures for subsequent plasmid analysis. Plates were then incubated at 37° C. for 18 hours. 8-10 individual clones were picked from plates and used as inoculums for 5 mL overnight cultures. Freezerstock was made at a concentration of 15% glycerol from individual clone cultures for future MBC confirmations. The plasmid DNA was extracted from individual clones and sent out of lab for sequence analysis (Macrogen).

Figure 2:
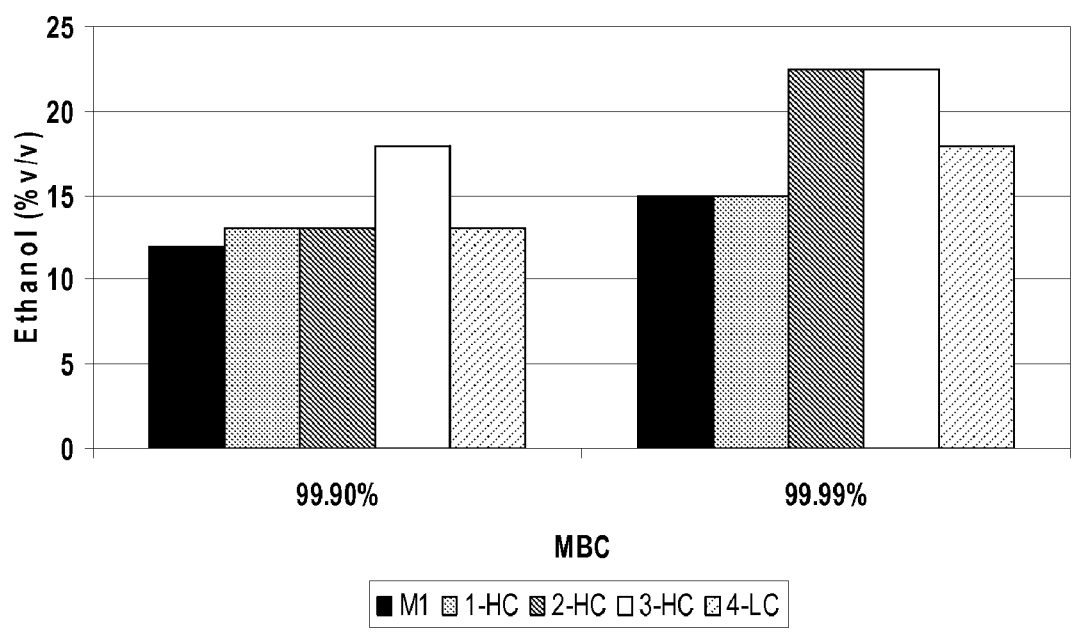
FIG. 2 is an exemplary graph illustrating the level of ethanol required to achieve 99.9 or 99.99% cell killing for different clones identified in these studies.

Five genomic libraries consisting of greater than $10^5$ clones were created with the high copy pEZseq and low copy pSMART vectors. Greater than 80% of the libraries were confirmed to contain inserts of the expected size. Libraries were transformed into MACH1 cells and greater than $10^7$ transformants were collected. These transformants were mixed and inoculated into MOPS minimal media with kanamycin and cultured in the presence of ethanol. Individual clones were chosen for sequencing (Table 1) and confirmation studies (FIG. 2). All four clones confer increased tolerance to ethanol for one or both values of the MBC when compared with the wild-type Mach1 (M1) MBC.

TABLE 1

Sequence Results and Gene Identification

| Clone #/ Copy Number | Position in Genome | Gene Name | Putative Function |
|---|---|---|---|
| 1-HC | 91,782-92,507 | ftsL1 | Cell division protein |
| 2-HC | 2,486,914-2,487,454 | yfdE | NAD-binding transferase |
| 3-HC | 3,603,260-3,603,993 | yhhL, yhhM | Hypothetical protein/receptor |
| 4-LC | 4,049,058-4,049,302 | csrC | RNA inhibitor of csrA |

The foregoing discussion has been presented for purposes of illustration and description. The foregoing is not intended to limit the form or forms disclosed herein. Although the description has included one or more embodiments and certain variations and modifications, other variations and modifications are within the scope of the embodiments, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/ or equivalent structures, functions, ranges or steps are disclosed herein, and without intending to publicly dedicate any patentable subject matter.

What is claimed is:

1. A modified Escherichia coli (E. coli) microorganism that has been modified to increase the expression of a gene selected from the group consisting of yfdE, yhhL, yhhM, and a combination thereof, whereby an alcohol tolerance is enhanced, said modified microorganism thereby having increased alcohol tolerance relative to its wild type.

2. The modified microorganism of claim 1, wherein said E. coli modified microorganism has minimum ethanol bactericidal concentration of at least about 17% v/v for 99.99%.

3. The E. coli of claim 1, wherein the alcohol is selected from the group consisting of ethylene glycol, propylene glycol, polyethylene glycol, polypropylene glycol, poly(ethylene glycol/propylene glycol), 1,3-propanediol, 1,2-butanediol, 2,3-butanediol, 1,4-butanediol, 1,6-hexanediol, pinacol, glycerol, neopentylglycol, pentaerythritol, meso-hydrobenzoin, 1,2-cyclopentanediol, 1,2-cyclohexanediol, methanol, ethanol, isopropanol, n-propanol, n-butanol, isobutanol, sec-butanol, tert-butanol, n-pentanol, isopentanol, amyl alcohol, tert-pentanol, cyclopentanol, cyclohexanol, n-hexanol, n-heptanol, n-octanol, n-nonanol. n-decanol, n-dodecanol n-tetradecanol, n-hexadecanol, n-octadecanol, phenoxyethanol, benzyl alcohol, diphenyl carbinol, tetraphenylcarbinol and a combination thereof.

4. The *E. coli* of claim 1, wherein the alcohol is ethanol.

5. The *E. coli* of claim 1, wherein the increased expression is accomplished through increased copy numbers of the gene.

6. The *E. coli* of claim 1, wherein the increased expression comprises enhanced upregulation of the gene.

7. A method for producing ethanol comprising: culturing a modified *Escherichia coli* (*E. coli*) microorganism under conditions sufficient to produce ethanol, wherein the microorganism has enhanced expression of a gene selected from the group consisting of yfdE, yhhL, and yhhM, and a combination thereof; and recovering ethanol from the culture.

8. The method of claim 7, wherein the increased expression is accomplished through increased copy numbers of the gene.

9. The method of claim 7, wherein the increased expression comprises enhanced upregulation of the gene.

10. A method for enhancing alcohol resistance of a modified *Escherichia coli* (*E. coli*) microorganism comprising modifying the microorganism to increase expression of a gene selected from the group consisting of yfdE, yhhL, and yhhM, and a combination thereof.

11. The method of claim 10, wherein the increased expression is accomplished through increased copy numbers of the gene.

12. The method of claim 10, wherein the increased expression comprises upregulation of the gene.

13. The method of claim 10, wherein the alcohol is ethanol.

* * * * *